US005392947A

United States Patent [19]
Gentile

[11] Patent Number: 5,392,947
[45] Date of Patent: Feb. 28, 1995

[54] DENTAL MOUTHWASH PRODUCT

[75] Inventor: James L. Gentile, Orange, Conn.

[73] Assignee: Chesebrough-Pond's USA Co., Division of Conopco, Inc., Greenwich, Conn.

[21] Appl. No.: 146,350

[22] Filed: Oct. 29, 1993

[51] Int. Cl.⁶ .............................................. B65D 1/04
[52] U.S. Cl. .................................... 220/665; 220/662; 215/6; 424/44; 222/129
[58] Field of Search ................... 206/524.1, 216, 219, 206/221; 220/662, 665; 215/6; 222/94, 129, 129.4, 142.3; 424/44, 49, 53

[56] References Cited

U.S. PATENT DOCUMENTS

| D. 190,101 | 4/1961 | Mangini . | |
|---|---|---|---|
| D. 288,526 | 3/1987 | Parad . | |
| 1,533,150 | 9/1925 | Dorsey et al. . | |
| 2,629,508 | 2/1953 | Prager | 206/221 |
| 2,661,870 | 12/1953 | Huenergardt . | |
| 2,661,871 | 12/1953 | Huenergardt . | |
| 2,756,129 | 7/1956 | Harris | 206/221 |
| 3,059,816 | 10/1962 | Goldstein . | |
| 3,729,553 | 4/1973 | Gold et al. . | |
| 4,687,663 | 8/1987 | Schaeffer . | |
| 4,837,007 | 6/1989 | Duckworth et al. . | |
| 4,964,539 | 10/1990 | Mueller . | |
| 5,143,261 | 9/1992 | Drobish . | |
| 5,147,072 | 9/1992 | Dirksing . | |
| 5,154,917 | 10/1992 | Ibrahim et al. . | |
| 5,252,312 | 10/1993 | Gentile et al. . | |
| 5,289,950 | 3/1994 | Gentile | 222/142.3 |

FOREIGN PATENT DOCUMENTS 944506  4/1949  France .

Primary Examiner—David T. Fidei
Attorney, Agent, or Firm—Milton L. Honig

[57] ABSTRACT

A dental mouthwash product is provided that includes a dispensing container with at least two discreet compartments. In a first of the compartments is a liquid component containing hydrogen peroxide. In a second of the compartments is a liquid component containing sodium bicarbonate. The hydrogen peroxide-containing compartment has an outer wall formed completely of opaque material. The compartment containing the sodium bicarbonate has an outer wall of a material whose clarity is sufficient to view the liquid level therewithin. A closure mechanism is sealingly attached to an upper end of the dispensing container. A structure for inhibiting gurgling of the liquid that can occur upon dispensing is provided in the form of either a vent pipe, a di7 vider wall or a U-shaped divider wall. Additionally, there is provided a child-proof mechanism in the form of a release-button controlling opening of a sealing cover on the closure mechanism.

14 Claims, 4 Drawing Sheets

DENTAL MOUTHWASH PRODUCT

BACKGROUND OF THE INVENTION

1. Field of the Invention

The invention concerns a packaged effervescible mouthwash composition which generates fresh effervescence at the time of use.

2. The Related Art

Effervescent mouthwash compositions, especially carbonated mouthwash, have been recognized as having desirable and advantageous dental properties. Special packaging is usually required. For instance, U.S. Pat. No. 3,729,533 (Gold et al) discloses an effervescent composition packaged in a two-compartment container. The first of these compartments is intended to store an alkaline solution such as aqueous sodium bicarbonate. The second of the compartments is intended to store an acid solution. During storage, each of the components are maintained separate from one another to prevent premature reaction. Upon dispensing, the components mix and thereby release carbon dioxide.

U.S. Pat. No. 4,687,663 (Schaeffer) describes a toothpaste having semi-solid bicarbonate and semi-solid hydrogen peroxide-containing components, each extruded from separate compartments and placed in contact on a toothbrush. When the brush is applied to teeth and gums, immediate mixing of the components occurs with rapid evolution of oxygen and carbon dioxide. The combination of the ingredients is believed to kill bacteria responsible for gum disease.

U.S. Pat. No. 5,154,917 (Ibraham et al) reports a mouthrinse product comprising a multi-compartment bottle with liquids of different colors stored therewithin. One of the liquids is alkaline containing sodium bicarbonate/carbonate. A second of the liquids is an acidic solution formed of citric acid. These red and blue liquids, respectively, upon dispensing from the bottle combine to form a liquid admixture of yet another color.

In copending U.S. patent application. Ser. Nos. 07/954,847, now U.S. Pat. No. 5,289,950 and 07/954,848, now U.S. Pat. No. 5,252,312, both filed Sep. 30, 1992, there is disclosed a packaged effervescible composition containing sodium bicarbonate and hydrogen peroxide active material, each in separate compartments of a dual-compartment dispenser. The dispenser includes a closure system comprising an inclined crown portion, at least two pouring spouts extending upwardly from an upper surface of the crown portion and a cover for securement to the crown portion. The cover is provided with depending plugs to close the closure. Each pouring spout is preferably provided with a vent opening in addition to product orifices in the spouts. The orifices can be positioned close together on the crown, all of which assists in achieving control over pouring.

Among problems of the known art is the tendency of one or a mixture of the components to drain back into the compartments and thereby spoil the contents. Secondly, the user of the package is given insufficient visual guidance on how to dispense the components from the package. As a result, unwanted premature mixing of materials may occur during pouring. This leads to reaction of the hydrogen peroxide and sodium bicarbonate outside of the mouth with no beneficial oxygen evolution. Thirdly, known packaging for dispensing from a multi-compartment dispenser is not adapted for uniform pouring of the components into small-mouth cups of the type typically used for mouthwash.

Even with the improvements of the copending applications, there have remained certain problems. For instance, hydrogen peroxide has been identified as storage unstable in a transparent container when exposed to light. On the other hand, light-excluding opaque containers have proved to be unsatisfactory. Opacity hinders a person's ability to accurately and controllably dispense relatively equal volumes from a dual-compartment dispenser. Transparent walled containers also serve as a window function for gauging the amounts of liquid remaining in the dispenser.

A further problem with the technology reported in the copending applications is that the vent holes are only partially successful in preventing "glugging" and uneven pouring. The "glugging" problem arises when the dispenser is tilted beyond the horizontal, especially when the container is full and is turned upside down.

Another problem with the dispenser as disclosed in the copending applications concerns the relatively large cover which obscures, at least to some extent, a view of the pouring operation. Pouring requires a certain amount of careful control to assure dispensing of equal volumes of each of the components.

Accordingly, it is an object of the present invention to provide a packaged effervescible composition with improved stability against premature light-induced decomposition of hydrogen peroxide while at the same time maintaining visibility of the liquids to be dispensed.

It is another object of the present invention to provide a packaged effervescible composition that eliminates "glugging" even under the most acute circumstances.

It is still another object of the present invention to provide a packaged effervescible composition with an improved line-of-sight that is unincumbered by such features as the cover of the dispenser.

It is a further object of the present invention to provide a packaged effervescible composition wherein the package has improved stability against toppling over from the standing position.

These and other objects of the present invention will become more readily apparent upon consideration of the foregoing summary, drawings and detailed description.

SUMMARY OF THE INVENTION

A dental mouthwash product is provided including:
(i) a first liquid component comprising hydrogen peroxide;
(ii) a second liquid component comprising sodium bicarbonate; and
(iii) a dispensing container including:
  at least two discreet compartments each with an upper outlet end, a first of the at least two discreet compartments being formed completely of opaque material, a second of the at least two discreet compartments having an outer wall being of a clarity sufficient to view a liquid level therein, the first compartment storing the first liquid component that includes hydrogen peroxide, and the second compartment storing the second liquid which includes sodium bicarbonate; and
  a closure mechanism for closing the compartments over the outlet ends.

Ordinarily, mouthwash products have been packaged in clear containers. According to the present invention, a package is provided with an opaque compartment for storing the hydrogen peroxide-containing first liquid component. The opaque walls insure against decomposition of the peroxide. On the other hand, the second compartment is formed of an outer wall having sufficient clarity to allow viewing of the liquid level of the second liquid component, the one containing sodium bicarbonate. In this format, there is achieved stability against degradation while at the same time allowing viewing of the liquid level to aid in accurate dosing.

A pedestal shoe is provided on a front face of the package. The shoe assists the generally elongated package in remaining stably upright in the storage mode.

A closure device is provided that improves visibility for a user during the dispensing procedure. Closure systems have often been provided with caps whose cover occupied the full breadth of the closure width. Herein is provided a cover whose area ranges over not greater than 80% of the area covered by an upper surface of the closure cap.

Below the cover is a crown portion to which the cover is hingedly attached. The crown portion may be oriented in a horizontal plane relative to a base surface of the package or, preferably may be oriented in an inclined position thereto. Around an outer edge of the crown portion is a peripheral skirt portion oriented downward toward the base of the package.

A pair of pouring spouts are situated adjacent one another extending upward from the crown portion. Preferably the pouring spouts are inclined so as to effect a pouring tip at the lower end of the spout. Within each spout is a dispensing opening and a vent opening, the latter being oriented between the former and a rear edge of the crown portion that hingedly attaches to the cover. On an undersurface of the crown portion are first and second interior skirt portions oriented downward for engaging an outer surface of the container in a fluid-tight manner.

On an undersurface of the cover are provided a pair of dispensing opening plugs and vent opening plugs. These plugs are so positioned and of such diameter to securely fit within the respective dispensing and vent openings upon the cap being pressed downward onto the pouring spouts to seal the closure.

A child-proof safety mechanism is provided on the closure in the form of a release button positioned on a front face of the closure. A closure prong situated along a peripheral edge of the cover can engageably communicate with an engagement area between the release button and the peripheral skirt portion.

"Gurgling" has been noted as a problem, especially when containers even with vent openings are relatively full and are emptied by being turned upside down. According to the present invention there is provided the further feature of a vent pipe or tube coterminous with the vent opening. The vent pipe extends from the vent opening downwardly toward a base of the container and has a length at least twice, preferably more than four times a diameter of the dispensing opening. An alternate embodiment for the prevention of "gurgling" may be provided in the form of a vertical divider wall oriented downwardly toward the container base and separating the dispensing from the vent opening. A second alternate embodiment of the device for inhibiting gurgling is through a U-shaped wall coterminous with the vent opening and projecting downwardly toward the base of the container. This embodiment is, essentially, a partially cut-away vent pipe as aforedescribed.

BRIEF DESCRIPTION OF THE DRAWINGS

The present invention will be better understood from the following description in conjunction with the accompanying drawings wherein.

DETAILED DESCRIPTION

For ease of description, the article of this invention is described in an upright position, and terms such as upper, lower, inclined, etc. are used with reference to this position. It will be understood, however, that the article of this invention may be manufactured, stored, transported and sold in an orientation other than the position described.

Figure 1:
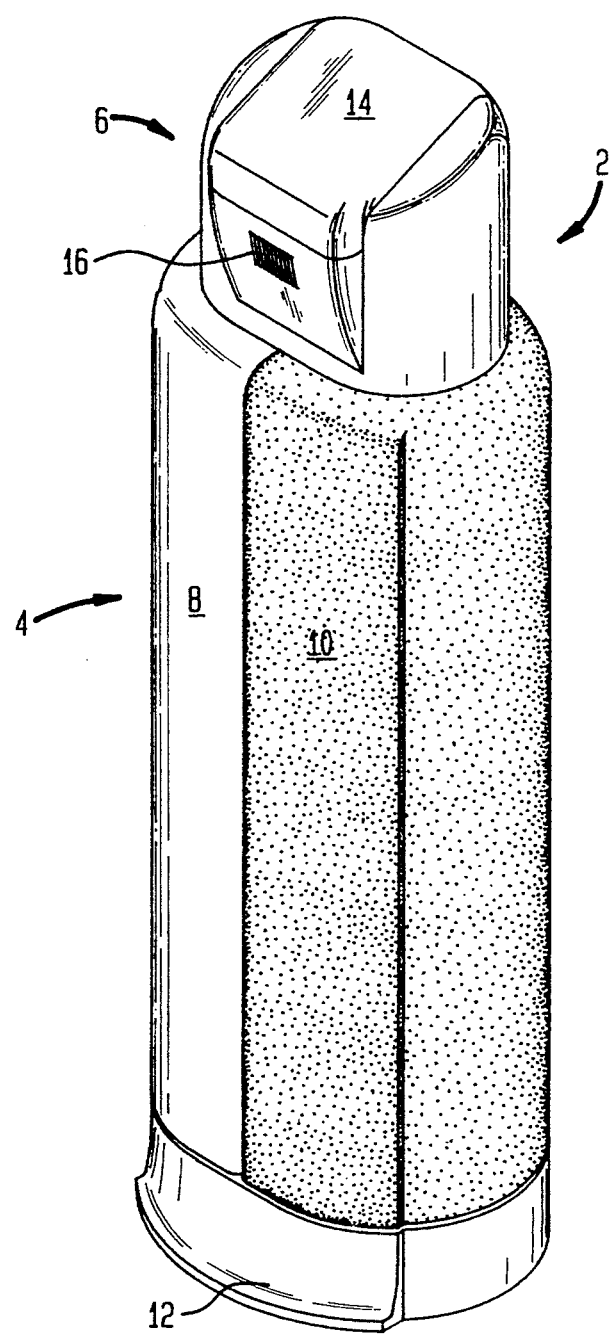
FIG. 1 is a perspective view of the package according to the present invention shown with a cover in the closed position.

FIG. 1 illustrates the package 2 utilized with the dental mouthwash product according to the present invention. Package 2 includes a container 4 and a closure 6. Container 4 is provided with separate storage compartments 8, 10. The first of these compartments 8 has outer walls formed of an opaque material, preferably a white plastic. On the other hand, the second compartment has outer walls formed of at least a translucent, preferably a clear, material transmitting light sufficient to view a liquid level therewithin. For instance, walls of the second compartment can be formed of a clear, blue-tinted plastic material.

Figure 4:
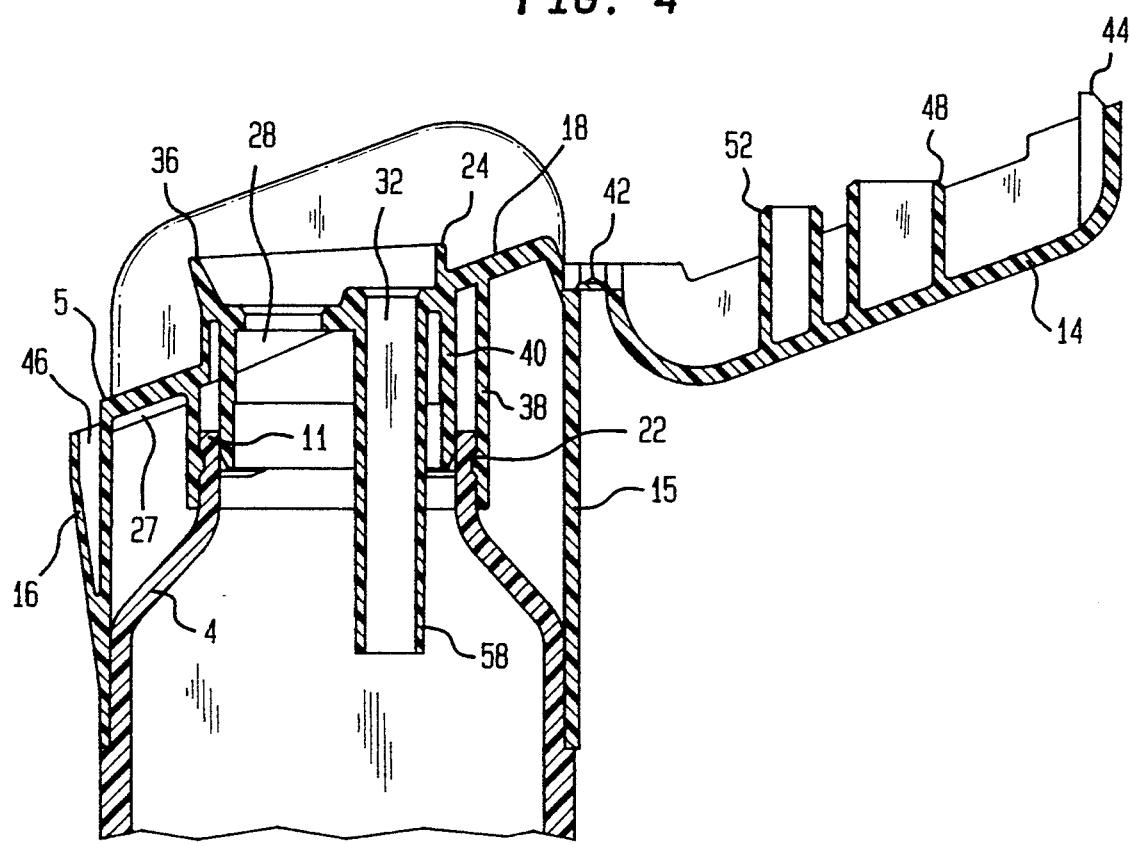
FIG. 4 is a fragmentary, cross-sectional view of the closure taken along line 4—4 of FIG. 2.

Each of the compartments 8, 10 terminate upwardly at an outlet end 11 as shown in FIG. 4. The two-compartment container 4 can either be formed of two entirely separate compartments 8 and 10 which are held together by closure 6 as shown in FIG. 1 or can be formed by a dividing wall in the container.

Adjacent a base of container 4 is a pedestal with a shoe 12 jutting outward. Pedestal shoe I 2 provides added stability to package 2 so that it remains stable against toppling when in a storage situation.

Figure 2:
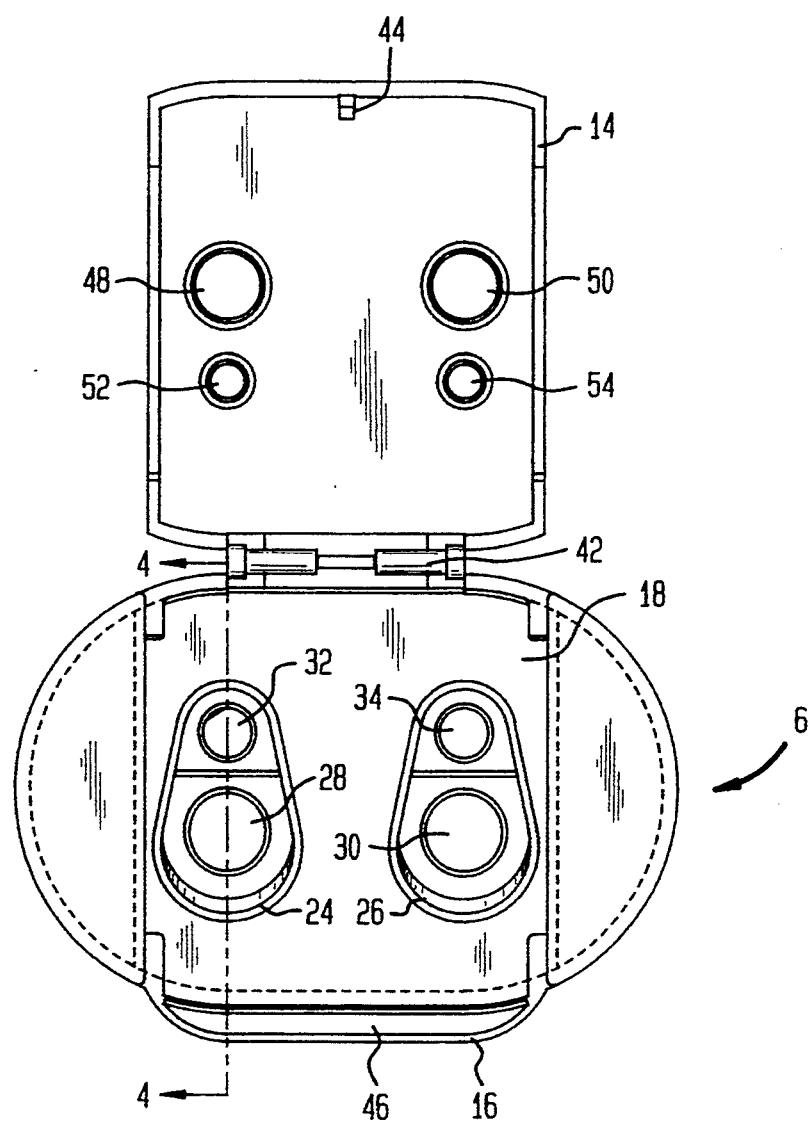
FIG. 2 is a top plan view showing the closure of the package with the cover in the open position.
Figure 3:
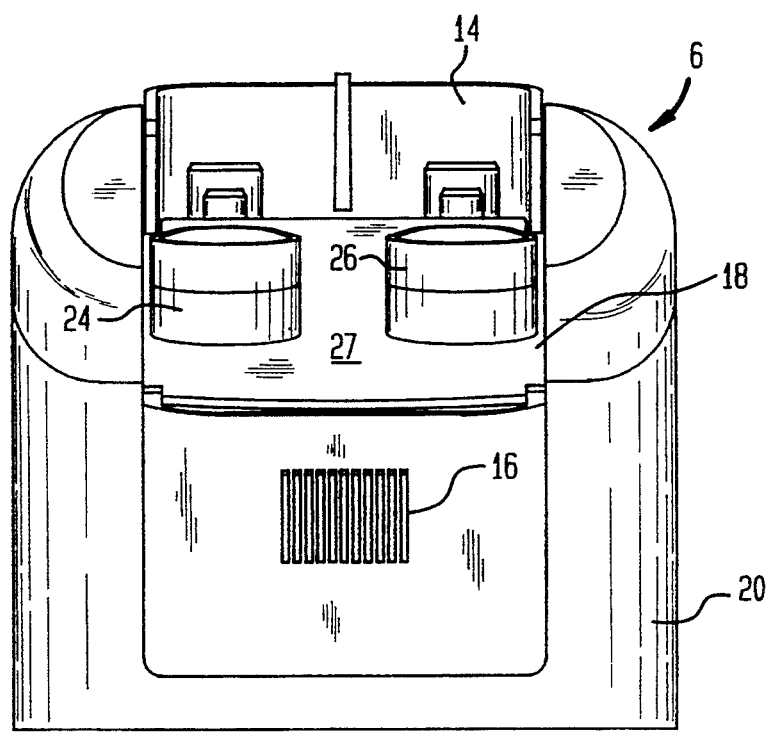
FIG. 3 is a perspective view showing the closure of the package with the cover in the open position.

FIGS. 2 and 3 illustrate various features of closure 6. These include an inclined crown portion 18 having a peripheral skirt portion 20. The peripheral skirt portion 20 is oriented downwardly toward container 4 from an outer edge 5 of the crown portion. Two pouring spouts 24, 26 extend upwardly from an upper surface 27 of the crown portion 18. Within each of the pouring spouts is a dispensing opening 28, 30 providing a through-going passage from the spout to a respective compartment of the container. Each spout is further provided with a vent opening 32, 34 which extends through the crown portion 18 and provides a communication passage between the spout and a respective compartment of the container. Each pouring spout 24, 26 is inclined to effect a pouring tip 36 as best shown in FIG. 4.

Additional to peripheral skirt portion 20, the inclined crown portion 18 on an undersurface 21 thereof includes a first and second interior skirt portion 38 and 40, respectively, downwardly directed. As shown in FIG. 4, the interior skirt portions 38, 40 engage an inner surface of container 4 in a fluid-tight manner. An inwardly projecting annular protrubence bead 22 formed on interior skirt portion 38 assists in achieving this engagement with container 4. Of course, any other ring or engagement mechanism may be suitable to accomplish the engagement function.

As best illustrated in FIGS. 2 and 3, closure 6 further includes a cover 14 pivotally attached through a hinge 42 at a rear edge of crown portion 18.

On an inner surface of cover 14 along a peripheral edge opposite to that bearing hinge 42 is a closure prong 44. In a sealing position of cover 14, the closure prong 44 will engage within engagement area 46 formed between a release button 16 and the peripheral skirt portion 20. Pressure applied against the face of release button 16 permits release of closure prong 44 from its catch mechanism. In the open position, cover 14 is maintained by hinge 42 in a retracted position sufficient to aid visibility in dispensing of the liquids and allow for pouring with one hand. It will be appreciated that cover 14 may be resealably attached to the crown portion by many known alternative means other than through a hinge.

Cover 14 on an undersurface thereof is provided with a pair of dispensing opening plugs 48, 50 and a pair of vent opening plugs 52, 54. These plugs are so oriented and dimensioned that they sealingly fit within the respective dispensing openings 28, 30 and vent openings 32, 34.

When cover 14 is in an open position, liquid in compartments 8 and 10 can simultaneously be dispensed by tilting package 2 to a substantially horizontal position. Thereby the liquids flow from pouring spouts 24, 26 over a lower edge of the crown portion 18. Each of the liquids flow by gravity from container 4 in a substantially uniform flow.

A special feature according to the present invention is a mechanism for inhibiting gurgling of liquid as liquid is dispensed through pouring spouts 24, 26. A preferred embodiment of the antigurgling mechanism is a vent pipe 58. A separate vent pipe is formed coterminous with each vent opening 32, 34 and extends downwardly into container 4. Vertical length of vent pipe 58 is preferably at least twice the diameter of dispensing opening 28, optimally at least four times the aforementioned diameter.

Figure 5:
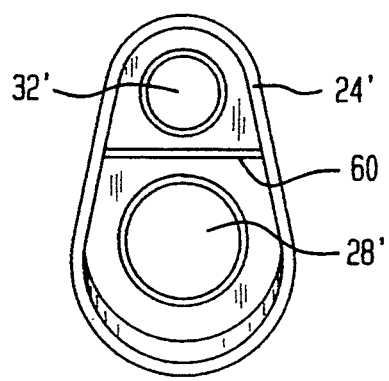
FIG. 5 is a fragmentary, top plan view of the spout area showing an alternate embodiment of the vent arrangement.

FIG. 5 illustrates a second embodiment of the mechanism for inhibiting gurgling of liquid dispensing from container 4. Instead of vent pipe 58, there is provided a divider wall 60 to separate dispensing opening 28' from vent opening 32'. Divider wall 60 may extend downwardly into container 4 a distance at least twice a diameter of the dispensing opening 28'.

Figure 6:
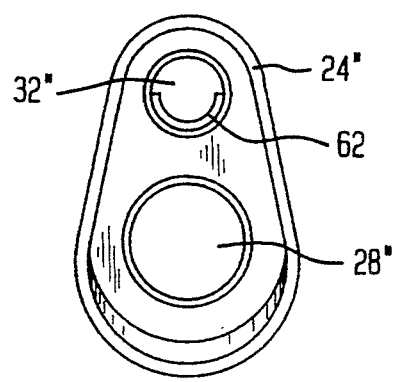
FIG. 6 is a fragmentary, top plan view of the spout area showing a second alternate embodiment of the vent arrangement.

FIG. 6 illustrates a third embodiment of the mechanism for inhibiting gurgling of liquid as it dispenses from container 4. In this embodiment, vent pipe 58 is replaced by a U-shaped divider wall 62 coterminous with vent opening 32" and extends downwardly in a manner and distance similar to that of vent pipe 58.

Packages according to the present invention are preferably constructed of plastics material. Preferably, closure 6 is formed from a more flexible plastic than that from which container 4 is formed. For instance, closure 6 can be manufactured from polyethylene or polypropylene while container 4 can be formed from a much harder plastic such as polyethylene terephthalate. These differences in plastic aid in friction fitting together the container with the closure.

The present invention thus provides a packaged effervescible mouthwash composition comprising a first liquid component including hydrogen peroxide as a functional ingredient and a second liquid component including sodium bicarbonate as a functional ingredient. Preferably the first liquid component comprises from 0.5 to 10% by weight hydrogen peroxide, more preferably 1 to 5%. The term "hydrogen peroxide" is herein defined as including hydrogen peroxide itself or any peroxide generator such as urea peroxide, zinc peroxide, calcium peroxide, sodium percarbonate and the like. The second liquid component preferably comprises from 1 to 20% by weight sodium bicarbonate, more preferably 2 to 5%.

Other oral hygiene medicaments suitable for use in a mouthwash product may be used in the present invention, such as anti-caries agents, anti-calculus agents, antiplaque agents, antimicrobial agents and combinations thereof.

Suitable anticaries agents include fluoride ion sources, such as alkali metal fluorides, alkali metal monofluorophosphates, stannous fluoride, most preferably sodium fluoride. Fluoride ion sources may be used in an amount sufficient to provide from about 25 ppm to about 1000 ppm fluoride based on the total weight of the mouthwash.

Suitable anti-calculus agents include the linear molecular dehydrated polyphosphate salts, including alkali metal tripolyphosphates and pyrophosphates. Suitably, the polyphosphate anti-calculus agent may be used in an amount of up to about 5%, preferably from about 0.5 to about 2%, by weight, based on the total weight of the mouthwash.

The packaged effervescible mouthwash composition may include any suitable conventional ingredients. The ingredients commonly employed in mouthwash compositions include, for example, flavoring agents, anti-foam agents, alcohols, antimicrobial agents, sweetening agents, surface active agents, deodorizing agents, coloring agents, bactericidal agents, astringent agents and the like. Any number of the foregoing ingredients, as well as other conventional ingredients, may be present in the compositions of this invention.

Generally, the mouthwash of the invention will comprise from about 45 to about 95% by weight of water, based on the total weight of the mouthwash.

Conventional manufacturing techniques may be used to prepare the package and mouthwash of the invention.

The present invention is illustrated in terms of its preferred embodiments in the accompanying Examples. All parts and percentages referred to in this specification are by weight, based upon the total weight of the mouthwash, unless otherwise specified.

EXAMPLE

A hydrogen peroxide containing liquid and a sodium bicarbonate containing liquid were prepared by admixing the following ingredients:

| Ingredients | H₂O₂ Liquid | NaHCO₃ |
|---|---|---|
| Deionized water | balance | balance |
| Ethanol | | 24 |
| Humectant (Polyol 2) | | 7 |
| Solubilizer (Polysorbate) | | 0.4 |
| Flavor | | 0.4 |
| Sodium bicarbonate | | 2 |
| Hydrogen peroxide (35% sol.) | 4.285 | |
| Dye | 0.0025 | |
| Saccharin | | 0.065 |
| Sodium lauryl sulphate | | 0.6 |
| Phosphoric acid | 0.04 | |

Equal amounts of the liquids were added to compartments 8 and 10 of a package of the type shown in FIGS. 1 to 3. The liquids after being dispensed from the package combined to form an effervescent mouthwash.

What is claimed is:

1. A dental mouthwash product comprising:
   (i) a first liquid component comprising hydrogen peroxide;
   (ii) a second liquid component comprising sodium bicarbonate; and
   (iii) a dispensing container comprising:
      at least two discreet compartments each with an upper outlet end, a first of the at least two discreet compartments being formed completely of opaque material, a second of the at least two discreet compartments having an outer wall being of a clarity sufficient to view a liquid level therein, the first compartment storing the first liquid component that includes hydrogen peroxide, and the second compartment storing the second liquid which includes sodium bicarbonate; and
      a closure mechanism for closing the compartments over the outlet ends.

2. The product according to claim 1 wherein the first liquid component comprises from 0.5 to 10% by weight of hydrogen peroxide.

3. The product according to claim 1 wherein the second liquid component comprises from 1 to 20% by weight of sodium bicarbonate.

4. The product according to claim 1 wherein each compartment contains about an equal quantity of liquid component stored therein and a closure means for allowing the first and second liquid components to be simultaneously dispensed from said compartments in about equal amounts.

5. The product according to claim 1 wherein the closure means further comprises:
   a crown portion having an upper surface, an under surface underneath the upper surface and a peripheral skirt portion depending downwardly from an outer edge of the crown portion, the peripheral skirt portion being of sufficient size to engage a surface of the container in a fluid-tight manner; at least two pouring spouts extending upwardly from the upper surface of the crown portion; each pouring spout being provided with a dispensing opening and a vent opening, each of which openings communicate through the crown portion and into one of the at least two compartments; and
   a cover for sealing the crown portion and attached thereto.

6. The product according to claim 5 wherein each vent opening is positioned between the respective dispensing vent and an upper edge of the crown portion.

7. The product according to claim 6 further comprising a means for inhibiting gurgling of liquid when the liquid components are dispensed from the container.

8. The product according to claim 7 wherein the means for inhibiting gurgling is a vent pipe coterminous with the vent opening and extending downward toward the container.

9. The product according to claim 8 wherein the vent pipe has a length at least twice that of a diameter of the pouring spout.

10. The product according to claim 7 wherein the means for inhibiting gurgling is a divider wall extending downwardly from the undersurface of the crown portion and separates the dispensing opening from the vent opening.

11. The product according to claim 7 wherein the means for inhibiting gurgling is a U-shaped divider wall coterminous with the vent opening and extending downward toward the container.

12. The product according to claim 1 wherein the first of the at least two discreet compartments is formed of a transparent wall tinted blue and the second of the at least two discreet compartments has an outer wall that is opaque and white in color.

13. The product according to claim 1 wherein the cover has an area smaller than an area of an upper surface of the closure means.

14. The product according to claim 5 further comprising a release button on the peripheral skirt portion, an engagement area being formed inward of the release button and of a geometry for receiving a closure prong formed on an outer edge of the cover.

* * * * *